United States Patent
Oki et al.

(10) Patent No.: US 9,150,883 B2
(45) Date of Patent: Oct. 6, 2015

(54) STRAIN OF THERMOANAEROBACTERIUM THERMOSACCHAROLYTICUM AND MUTANT THEREOF

(75) Inventors: Yasuhiro Oki, Suruga-ku (JP); Yutaka Mitani, Yaizu (JP)

(73) Assignee: SAPPORO BREWERIES LIMITED, Tokyo (JP)

( * ) Notice: Subject to any disclaimer, the term of this patent is extended or adjusted under 35 U.S.C. 154(b) by 1039 days.

(21) Appl. No.: 12/528,468

(22) PCT Filed: Jan. 25, 2008

(86) PCT No.: PCT/JP2008/051057
§ 371 (c)(1),
(2), (4) Date: Aug. 25, 2009

(87) PCT Pub. No.: WO2008/120486
PCT Pub. Date: Oct. 9, 2008

(65) Prior Publication Data
US 2010/0035328 A1    Feb. 11, 2010

(30) Foreign Application Priority Data
Mar. 29, 2007   (JP) ................... 2007-089430

(51) Int. Cl.
*C12P 3/00* (2006.01)
*C12R 1/01* (2006.01)

(52) U.S. Cl.
CPC .... *C12P 3/00* (2013.01); *C12R 1/01* (2013.01)

(58) Field of Classification Search
CPC ......... Y02E 50/16; Y02E 50/17; Y02E 50/10; Y02E 50/18; Y02E 50/32; Y02E 50/343; C12P 7/10; C12P 19/02; C12P 7/08; C12P 19/14; C12P 2203/00; C12P 7/065; C12P 2201/00; C12P 7/06; C12P 7/20; C12P 13/001
See application file for complete search history.

(56) References Cited

U.S. PATENT DOCUMENTS 2,641,566 A  *  6/1953  Zobell ........................... 435/281
7,968,322 B2 *  6/2011  Atsumi et al. ................. 435/168

FOREIGN PATENT DOCUMENTS

JP        64-23890    *  1/1989
JP        4 169178       6/1992

OTHER PUBLICATIONS

Ueno, Y. et al., "Changes in Bacterial Community During Fermentative Hydrogen and Acid Production From Organic Waste by Thermophilic Anaerobic Microflora", Journal of Applied Microbiology, vol. 101, No. 2, pp. 331-343 (2006).
Abe, T. et al., "Biomass Seipan Haikibutsu Kara No Suiso Seizo", Environmental Solution Technology, vol. 6, No. 2, pp. 17-21 (2007).
Chinese Office Action issued Mar. 23, 2011, in Patent Application No. 200880008324.2 (with partial English-language translation).

* cited by examiner

*Primary Examiner* — Debbie K Ware
(74) *Attorney, Agent, or Firm* — Oblon, McClelland, Maier & Neustadt, L.L.P.

(57) ABSTRACT

A microorganism suitable for production of hydrogen that is a *Thermoanaerobacterium thermosaccharolyticum* strain with an accession number of FERM BP-10793, or its mutants.

11 Claims, 3 Drawing Sheets

STRAIN OF THERMOANAEROBACTERIUM THERMOSACCHAROLYTICUM AND MUTANT THEREOF

CROSS-REFERENCE TO RELATED APPLICATIONS

This application is a national-stage filing under 35 U.S.C. §371 of PCT/JP08/051057, filed Jan. 25, 2008, which claims priority to Japan 2007-089430, filed Mar. 29, 2007.

TECHNICAL FIELD

The present invention relates to a novel microorganism, in particular, a novel microorganism capable of producing hydrogen.

BACKGROUND ART

Hydrogen has attracted attention as an energy source that can be used for fuel cells or the like. One method of producing hydrogen is hydrogen fermentation using a microorganism capable of producing hydrogen (for example, Patent Document 1).

Patent Document 1: JP 04-169178 A

DISCLOSURE OF THE INVENTION

Problems to be Solved by the Invention

However, microorganisms used in conventional hydrogen fermentation have insufficient ability to produce hydrogen at a low pH range. In addition, in the conventional hydrogen fermentation, the ability to produce hydrogen is lowered in some cases due to contamination.

On the other hand, the inventors of the present invention have made extensive studies and discovered a novel microorganism suitable for production of hydrogen, thus the present invention has been completed.

Means for Solving the Problems

A microorganism according to one embodiment of the present invention is characterized by being a *Thermoanaerobacterium thermosaccharolyticum* strain deposited at the International Patent Organism Depositary, National Institute of Advanced Industrial Science and Technology (AIST Tsukuba Central 6, 1-1, Higashi 1-chome Tsukuba-shi, Ibaraki-ken 305-8566 Japan) on Mar. 2, 2007 with an accession number of FERM BP-10793. Meanwhile, a microorganism according to one embodiment of the present invention is a mutant of the *Thermoanaerobacterium thermosaccharolyticum* strain with an accession number of FERM BP-10793, and is characterized by being capable of producing 270 mL or more of hydrogen from 1 g of a sugar when cultured at a pH in the range of 4.5 or higher and 6.5 or lower. In particular, the microorganism is characterized by being capable of producing 270 mL or more of hydrogen from 1 g of a sugar when cultured at a pH in the range of 5.0 or higher and 6.0 or lower. In addition, a microorganism according to one embodiment of the present invention is a mutant of *Thermoanaerobacterium thermosaccharolyticum* strain with an accession number of FERM BP-10793 and is characterized by producing hydrogen at a molar ratio of 2.1 or more based on xylose when cultured in a medium containing xylose as a sugar source at a pH in the range of 4.5 or higher and 6.5 or lower. In particular, the microorganism is characterized by being capable of producing hydrogen at a molar ratio of 2.1 or more based on xylose when cultured in a medium containing xylose as a sugar source at a pH in the range of 4.8 or higher and 5.5 or lower. According to the present invention, it is possible to provide a novel microorganism suitable for the production of hydrogen.

BEST MODE FOR CARRYING OUT THE INVENTION

Figure 1:
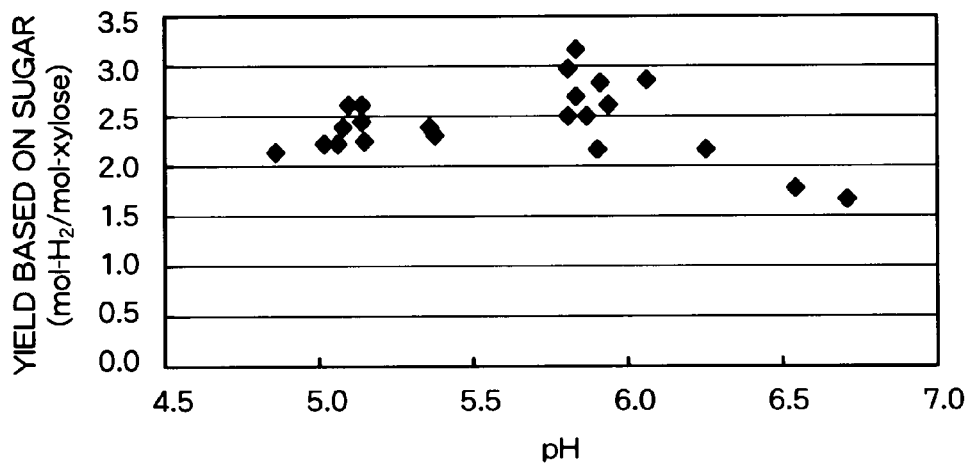
FIG. 1 is a graph showing hydrogen productivity at various pHs of a microorganism according to one embodiment of the present invention.

Hereinafter, a microorganism according to one embodiment of the present invention will be described. Note that the microorganism according to the present invention is not limited to one illustrated in this embodiment.

A microorganism according to this embodiment (hereinafter, referred to as "microorganism of the present invention") includes *Thermoanaerobacterium thermosaccharolyticum* strain with an accession number of FERM BP-10793 (hereinafter, referred to as "strain PEH9") and a mutant thereof. The microorganism of the present invention is gram-positive and obligately-anaerobic and rod-shaped.

The microorganism of the present invention can produce hydrogen by sugar metabolism. That is, the microorganism of the present invention can produce from sugars an organic acid such as acetic acid or butyric acid and can produce a gas (hereinafter, referred to as "fermentation gas") containing carbon dioxide and hydrogen in a culture solution.

The sugar that may be used in production of hydrogen by the microorganism of the present invention is not particularly limited, and for example, a sugar in a plant biomass or a waste food may be used. Specifically, there may be used polysaccharides (such as starch and cellulose), oligosaccharides, disaccharides, and monosaccharides (such as xylose and glucose).

The microorganism of the present invention can produce hydrogen at a wide range of pHs, and the microorganism can efficiently produce hydrogen at a low pH range. That is, the microorganism of the present invention can produce hydrogen at a pH in the range of 4.5 or higher and 7.0 or lower, preferably in the range of 4.8 or higher and 5.5 or lower, particularly preferably in the range of 5.0 or higher and 5.2 or lower. In the case where the pH is lower than 4.5, and in the case where the pH is higher than 7.0, the hydrogen production efficiency of the microorganism of the present invention is lowered.

On the other hand, if hydrogen fermentation using the microorganism of the present invention is performed at pH 5.5 or lower, the occurrence of contamination caused by other microorganisms producing no hydrogen can be effectively suppressed. For example, many methane fermentation microorganisms have a lowered ability to produce methane at a pH lower than 7.0, and therefore use of the microorganism of the present invention enables the suppression of contamination of methane fermentation microorganisms in hydrogen fermentation.

For example, in a two-step fermentation system for performing hydrogen fermentation in a first fermenter and for performing methane fermentation in a second fermenter using the effluent obtained after the hydrogen fermentation in the first fermenter, the hydrogen fermentation in the first fermenter is performed using the microorganism of the present invention at pH 5.5 or lower. This can effectively suppress production of methane by a methane fermentation microorganism in the first fermenter, to thereby produce a fermentation gas with high content of hydrogen in the first fermenter even if an interfusion of a methane fermentation microorganism occurs in the first fermentation.

For example, in a fuel production system including a pretreatment step for decomposing a plant biomass to produce a biofuel such as ethanol upstream of the hydrogen fermentation step, an acid is used in some cases in the pretreatment step to decompose lignocellulosic biomass in the biomass into low-molecular-weight sugars such as monosaccharide or disaccharide. In this case, a culture solution containing a residue acidified in the pretreatment step is supplied to the hydrogen fermentation, but use of the microorganism of the present invention in the hydrogen fermentation can effectively reduce the amount of a neutralizer to be added to the culture solution compared with the conventional methods.

In the case where hydrogen fermentation is performed using the microorganism of the present invention at a low pH range, it is expected to promote the release of hydrogen produced in cells of the microorganism of the present invention to the outside of the cells because of the relationship between the pH and oxidation-reduction potential.

In particular, the microorganism of the present invention can achieve a high ratio of produced hydrogen to a consumed sugar (amount of produced hydrogen/amount of consumed sugar) (hereinafter, referred to as "yield based on sugar") at a low pH range. That is, in the case of using xylose as a sugar to be added to a culture solution, the microorganism of the present invention can produce hydrogen at a yield based on sugar of 1.6 or more, which represents a ratio of the amount of hydrogen produced to the amount of xylose consumed in the culture medium (mol-$H_2$/mol-xylose), at a pH in the range of 4.5 or higher and 7.0 or lower.

In particular, the microorganism of the present invention can produce 2.1 mol or more of hydrogen from 1 mol of xylose in a culture solution at a pH in the range of 4.5 or higher and 6.5 or lower. That is, the microorganism of the present invention can produce hydrogen at a yield based on sugar of 2.1 or more.

Also, the microorganism of the present invention can produce hydrogen at a wide range of temperatures, and the microorganism can effectively produce hydrogen at a high temperature range. That is, the microorganism of the present invention can produce hydrogen at a temperature in the range of 37° C. or higher and 65° C. or lower, preferably in the range of 45° C. or higher and 60° C. or lower, more preferably in the range of 50° C. or higher and 60° C. or lower, particularly preferably in the range of 55° C. or higher and 60° C. or lower. In the case where the temperature is lower than 37° C., and in the case where the temperature is higher than 65° C., the hydrogen production efficiency of the microorganism of the present invention is lowered.

On the other hand, if the temperature is 55° C. or higher, the contamination caused by other microorganisms producing no hydrogen is effectively suppressed, and the hydrogen fermentation using the microorganism of the present invention can be effectively performed. If the temperature is 50° C. or higher, the effect of heat, generated in the step performed upstream of the hydrogen fermentation, on the hydrogen fermentation can be reduced.

That is, as described above, for example, in a fuel production system including a pretreatment step for producing a biofuel from biomass upstream of the hydrogen fermentation step, a lignocellulosic biomass may be decomposed in the pretreatment step by heating to 80 to 230° C. in the presence of an acid or an alkali. In this case, a culture solution containing a residue heated in the pretreatment step is supplied to the hydrogen fermentation, but use of the microorganism of the present invention in the hydrogen fermentation can omit operations for cooling the culture solution or can effectively reduce the operations compared with the conventional method.

The microorganism of the present invention can produce hydrogen under conditions obtained by arbitrarily combining a wide range of pHs and a wide range of temperatures, and in particular, the microorganism can efficiently produce hydrogen under conditions obtained by combining a lower pH and a higher temperature compared with a conventional microorganism for hydrogen fermentation.

That is, the microorganism of the present invention can produce hydrogen at a yield based on sugar of 2.1 or more under conditions of, for example, a pH in the range of 4.5 or higher and 6.5 or lower and a temperature in the range of 55° C. or higher and 60° C. or lower.

As described above, hydrogen fermentation using the microorganism of the present invention at a low pH and at a high temperature can extremely effectively suppress contamination of other microorganisms in the hydrogen fermentation and can effectively reduce operations for neutralizing or cooling a culture solution, which is performed for eliminating the effect of the biofuel-producing step provided on the upstream side, compared with a conventional method.

The microorganism of the present invention can easily autolyze under predetermined conditions. That is, for example, in the case where the concentration of a predetermined nutrient component in a culture solution is decreased to be lower than a predetermined value, the cell bodies of the microorganism of the present invention are easily destroyed.

Specifically, for example, in the case where the microorganism of the present invention is cultured in a culture solution containing xylose as a sugar source, the microorganism of the present invention may start to autolyze by reducing the concentration of xylose in the culture solution to 500 mg/L or less. Therefore, in the hydrogen fermentation using the microorganism of the present invention, the amount of residual sludge after completion of the hydrogen fermentation can be effectively reduced.

Hereinafter, hydrogen fermentation using the microorganism of the present invention will be described specifically.

Example 1

In Example 1, hydrogen fermentation was performed at various pHs. The strain PEH9 was used as a microorganism of the present invention. The control strains used were the strain PEH8 and ATCC strain 7956, the strain PEH8 being a *Thermoanaerobacterium thermosaccharolyticum* microorganism and different from the strain PEH9. The medium used was an aqueous solution containing 1.0% (w/v) of xylose, 0.4% (w/v) of yeast extract (Kyokuto Pharmaceutical Industrial Co., Ltd.), 0.25% (w/v) of MOPS, 0.091% (w/v) of $K_2HPO_4$, 0.03% (w/v) of $NaH_2PO_4$, 0.02% (w/v) of $MgCl_2$, 0.01% (w/v) of $CaCl_2$, 0.03% (w/v) of $(NH_4)_2SO_4$, 0.002% (w/v) of $FeSO_4$, 0.04% (w/v) of L-cysteine, and 0.11% (w/v) of resazurin.

Hereinafter, a process for obtaining the strain PEH9 and strain PEH8 will be described simply. That is, first, high-temperature anaerobically-digested sludge collected from a sewage treatment facility was acclimatized with brewery effluent for about one month, to thereby prepare a hydrogen fermentation flora capable of stably producing 50 to 60% of hydrogen and 40 to 50% of carbon dioxide. From the flora, 24 microorganism strains were isolated in a modified GAM medium (for isolation of anaerobic microorganisms, manufactured by Nippon Suisan Kaisya, Ltd.), and a strain that showed the highest hydrogen productivity was obtained as a strain PEH8. Thereafter, the strain PEH8 was irradiated with ultraviolet rays, to thereby prepare mutants.

Then, 12 microorganism strains capable of growing at pH 5.0 or lower were selected from 100,000 microorganism strains that had been subjected to the mutation treatment, and from the selected strains, one microorganism strain having excellent hydrogen fermentation ability was further selected as a strain PEH9.

On the other hand, ATCC strain 7956 is an existing microorganism strain that is the most closely related to the strain PEH8, which was proved by determination of the sequence of the entire region of 16SrDNA of the strain PEH8 and by a lineage analysis based on the sequence. A DNA-DNA hybrid formation test was performed three times to compare the strain PEH8 and ATCC 7956, and it revealed that the average homology level was 70% or more.

Then, the strain PEH9, strain PEH8, or ATCC strain 7956 was inoculated into 500 mL of a medium in a 1-L fermenter (BMJ-01, manufactured by ABLE & Biott Co., Ltd.) and a continuous culture under anaerobic conditions at dilution rates of 0.2 to 0.4 was performed.

The culture temperature was kept constant at 55° C. Meanwhile, the pH of the culture solution was changed in the range of 4.5 to 7.0 in a stepwise manner by automatic addition of sodium hydroxide into the culture solution.

Then, volumes of hydrogen produced by the strain PEH9, strain PEH8, or ATCC strain 7956 were estimated at various pHs in the range of 4.5 to 7.0. That is, the generated gas was collected using a Tedlar bag, and the volume of the fermentation gas generated per 24 hours was determined. The composition of the fermentation gas was analyzed using a gas chromatography apparatus (GC-14B, manufactured by Shimadzu Corporation) with a thermal conductivity detector (TCD), and the hydrogen production volume was calculated from a percentage of hydrogen in the fermentation gas. The gas chromatography analysis was performed using high-purity argon gas as a carrier gas, and using molecular sieve 5 Å and Polapack Q as column carriers, at an inlet temperature of 60° C., at a detector temperature of 80° C., and at a column oven temperature of 60° C. Moreover, the supernatants obtained by centrifuging (15,000 rpm, 10 minutes) the medium and culture solution were filtered with a membrane filter (pore size 0.2 μm), to thereby yield samples, and the samples were analyzed by high performance liquid chromatography with a fluorescence detector (reducing sugar analysis system, manufactured by Shimadzu Corporation) to determine xylose amounts in the medium and culture solution. The high performance liquid chromatography analysis was performed using a column (shim-pack ISA-07/S2504, 250 mm in length×4.0 mm in diameter, manufactured by Shimadzu Corporation) by a gradient elution with mobile phases from 100% of solution A (0.1 M potassium borate buffer) to 100% of solution B (0.4 M potassium borate buffer) at a flow rate of 0.6 mL/min and at a temperature of 65° C. Meanwhile, the detection of xylose was performed using a reaction agent containing 1% (w/v) of arginine and 3% (w/v) of boric acid at a flow rate of 0.5 mL/min and at a reaction temperature of 150° C. and the fluorescence detector with an excitation wavelength (Ex) of 320 nm and an emission wavelength (Em) of 430 nm. In addition, the density of microorganism cells in the culture solution at the time of the determination of the hydrogen production volumes was about $10^6$ to $10^7$ cells/mL.

Figure 2:
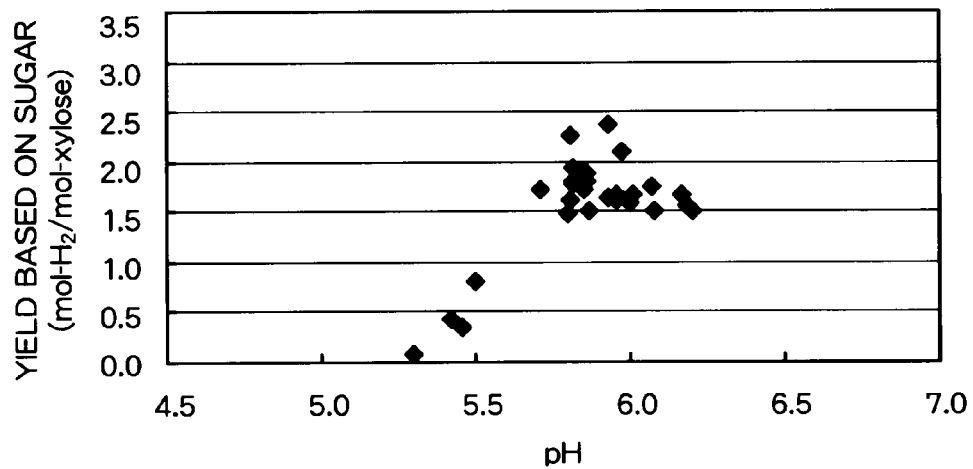
FIG. 2 is a graph showing the hydrogen productivity at various pHs of another microorganism used as a control.
Figure 3:
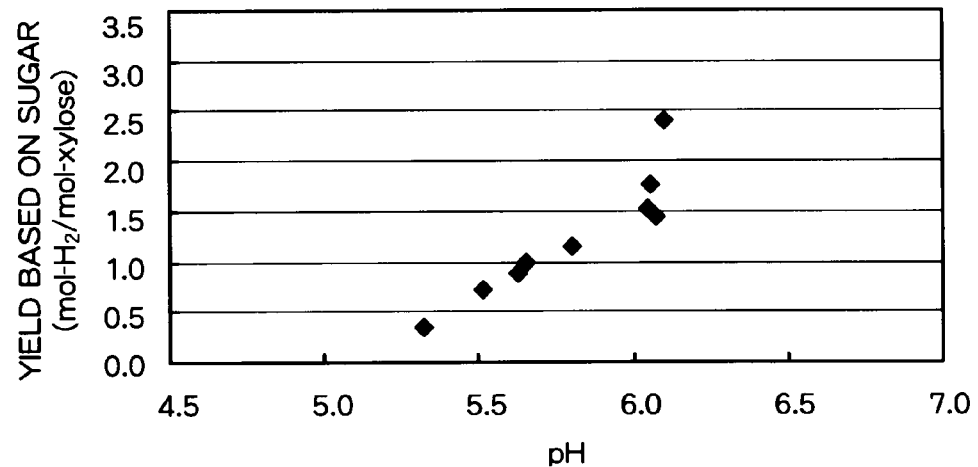
FIG. 3 is a graph showing the hydrogen productivity at various pHs of yet another microorganism used as a control.

FIGS. 1, 2, and 3 show the determination results of the hydrogen productivities of the strain PEH9, strain PEH8, and ATCC strain 7956, respectively. In FIGS. 1, 2, and 3, the abscissa axes represent the pH of the culture solution, and the ordinate axes represent the yield based on sugar (mol-$H_2$/mol-xylose).

As shown in FIG. 1, in the case of using the culture solution containing xylose as a sugar source, the strain PEH9 was found to grow well at a wide range of pHs (4.5 to 7.0) and produce hydrogen at a high yield based on sugar of 1.6 to 3.2 mol-$H_2$/mol-xylose. In particular, even at a low pH range of 4.8 to 5.5, the strain PEH9 was able to produce hydrogen at a relatively high yield based on sugar of 2.1 or more.

Specifically, in the cases of pH 4.86, 5.02, 5.06, 5.08, 5.10, 5.14, 5.15, 5.36, and 5.38, the strain PEH9 was able to produce hydrogen at yields based on sugar of 2.13, 2.23, 2.23, 2.38, 2.62, 2.61, 2.24, 2.40, and 2.31, respectively. In addition, in the cases of pH 5.86 to 6.25, the strain PEH9 was able to produce hydrogen at yields based on sugar of 2.13 to 3.16, and in the case of pH 6.54, the strain PEH9 was able to produce hydrogen at a yield based on sugar of 1.78.

On the other hand, as shown in FIG. 2, the yield based on sugar of the strain PEH8 was found to significantly decrease at pH 5.5 or less, and for example, the yield based on sugar at pH 5.50 was found to be 0.81. Meanwhile, as shown in FIG. 3, the yields based on sugar of the ATCC strain 7956 at pH 5.5 and 5.32 were found to be 0.73 and 0.36, respectively. As described above, the strain PEH9 was confirmed to efficiently produce hydrogen at a low pH range (for example, in the range of 4.8 or higher and 6.3 or lower).

Example 2

In Example 2, the hydrogen productivity at a pH in the range of 5.0 to 5.2 was confirmed on a 1-L scale. The strain PEH9 was used as a microorganism of the present invention. The medium used was an aqueous solution containing 1.0% (w/v) of xylose, 2% (w/v) of peptone, 0.5% (w/v) of yeast extract, 1.0% (w/v) of malt extract, 0.3% (w/v) of $K_2HPO_4$, 0.1% (w/v) of $MgSO_4$, 0.02% (w/v) of L-cysteine, 0.2% (w/v) of L-malic acid, 0.003% (w/v) of oleic acid, and 0.1% (w/v) of Tween 80. Then, the strain PEH9 was inoculated into 500 mL of the medium in a 1-L fermenter (BMJ-01, manufactured by ABLE & Biott Co., Ltd.) and a continuous culture was performed under anaerobic conditions at dilution rates of 0.3 to 0.4.

The culture temperature was kept constant at 55° C. Meanwhile, the pH of the culture solution was changed in the range of 5.0 to 5.2 in a stepwise manner by automatic addition of sodium hydroxide into the culture solution.

The proliferation of the strain PEH9 in the culture solution was confirmed to be stable, and then the fermentation gas production volumes per 24 hours in the five-day culture period and the compositions of the fermentation gas were determined by gas chromatography in the same way as Example 1, followed by calculation of hydrogen production volumes based on the results of the determination. The medium used in this example contains not only xylose but also a sugar derived from malt extract (such as maltose or glucose), and therefore a total sugar analysis for the medium and culture solution was performed by the phenol-sulfuric acid method to calculate sugar consumption. The yield based on sugar of hydrogen is shown as an amount of produced hydrogen per g of a consumed sugar in terms of a volume at standard conditions (standard environmental temperature and pressure: temperature 25° C., air pressure 1 bar).

Figure 4:
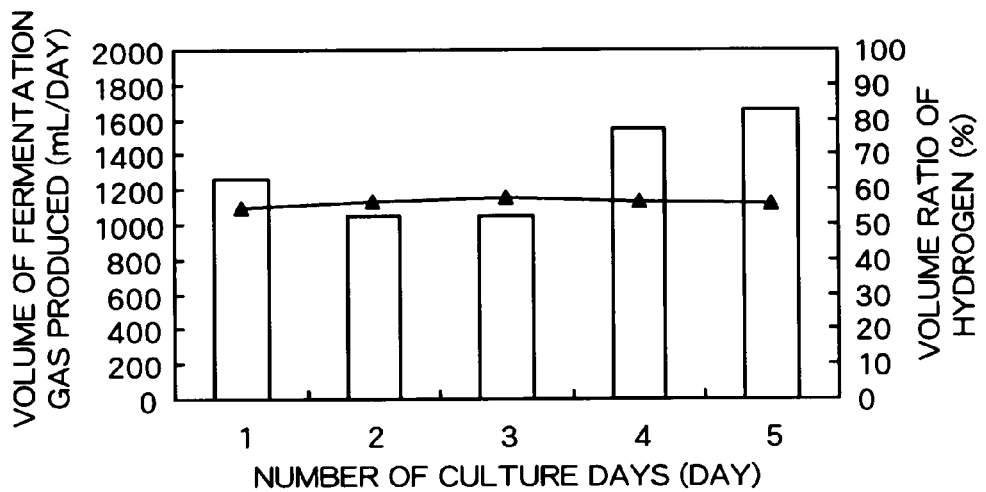
FIG. 4 is a graph showing the hydrogen productivity at pH 5.0 to 5.2 of a microorganism according to one embodiment of the present invention.

FIG. 4 shows the determination results of the hydrogen productivity of the strain PEH9. In FIG. 4, the abscissa axis represents the number of culture days (day), the left ordinate axis represents the volume of a fermentation gas produced for one day in the culture days (mL/day), the right ordinate axis represents the volume ratio of hydrogen in the fermentation gas (%), the open bars show the volumes of the fermentation gas, and triangles show the volume ratios of hydrogen.

As shown in FIG. 4, the strain PEH9 was able to stably produce a fermentation gas containing hydrogen over five days. Specifically, as average values for the five culture days, the volume of the fermentation gas produced was 1,312 mL/day, the volume ratio of hydrogen was 56.4%, the hydrogen production volume was 740 mL/day, the volume of the supplied culture solution was 154 mL/day, the total amount of sugars in the supplied culture solution was 16,200 mg/L, and the total amount of sugars in the discharged culture solution was 466 mg/L.

Moreover, the strain PEH9 was able to efficiently produce hydrogen at a yield based on sugar of 277 to 326 (average for five days: 306) mL-$H_2$/g-sugar at a pH in the range of 5.0 to 5.2. That is, the strain PEH9 was confirmed to produce hydrogen at a yield based on sugar of 270 mL-$H_2$/g-sugar or more at a pH in the range of 5.0 to 5.2.

Example 3

In Example 3, the hydrogen producing ability at a pH in the range of 5.8 to 6.0 was confirmed on a 1-L scale. The hydrogen fermentation was performed under the same conditions as those of Example 2 above, except for the pH range.

Figure 5:
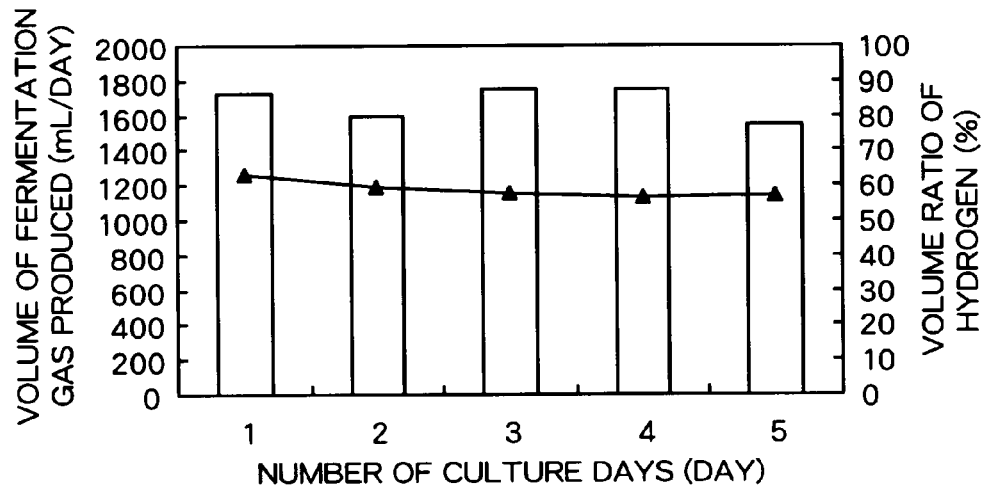
FIG. 5 is a graph showing the hydrogen productivity at pH 5.8 to 6.0 of a microorganism according to one embodiment of the present invention.

FIG. 5 shows the determination results of the hydrogen productivity of the strain PEH9. In FIG. 5, the abscissa axis represents the number of culture days (day), the left ordinate axis represents the volume of a fermentation gas produced for one day in the culture days (mL/day), the right ordinate axis represents the volume ratio of hydrogen in the fermentation gas (%), the open bars show the volumes of the fermentation gas, and triangles show the volume ratios of hydrogen.

As shown in FIG. 5, the strain PEH9 was able to stably produce a fermentation gas containing hydrogen over five days. Specifically, as average values for the five culture days, the volume of the fermentation gas produced was 1,676 mL/day, the volume ratio of hydrogen was 58.8%, the hydrogen production volume was 985 mL/day, the volume of the supplied culture solution was 179 mL/day, the total amount of sugars in the supplied culture solution was 16,200 mg/L, and the total amount of sugars in the discharged culture solution was 372 mg/L.

Moreover, the strain PEH9 was able to efficiently produce hydrogen at a yield based on sugar of 312 to 393 (average for five days: 348) mL-$H_2$/g-sugar at a pH in the range of 5.8 to 6.0. That is, together with the results in Example 2, the strain PEH9 was confirmed to produce hydrogen at a yield based on sugar of at least 270 mL-$H_2$/g-sugar at a pH in the range of at least 5.0 to 6.0.

Example 4

In Example 4, hydrogen fermentation was performed at various temperatures. The strain PEH9 was used as a microorganism of the present invention. The culture solution used was an aqueous solution containing 0.5% (w/v) of xylose, 1.6% (w/v) of tryptone, 1.0% (w/v) of yeast extract, and 0.4% (w/v) of sodium chloride.

Then, the strain PEH9 was inoculated into 20-mL vials each containing 10 mL of the culture solution, and the vials were sealed, followed by batch culture under anaerobic conditions at a temperature of 30° C., 37° C., 45° C., 55° C., 60° C., 65° C., or 70° C.

A syringe was injected to each vial 20 hours and 90 hours after the beginning of the culture to calculate a fermentation gas production volume, and the composition of the fermentation gas was determined by gas chromatography in the same way as Example 1, followed by calculation of a hydrogen production volume based on the results of the determination. Moreover, in order to evaluate the density of microorganism cells of the strain PEH9 in the culture solution, after the gas analysis, the turbidity of the culture solution (absorbance at a wavelength of 660 nm) was determined using a spectrophotometer. Note that in Example 4, the pH of the culture solution at the beginning of the culture was in the range of 6.0 to 6.5, and pH gradually decreased as the culture time elapsed, with the pH reaching 4.5 to 5.0 ninety hours after the beginning of the culture.

Figure 6:
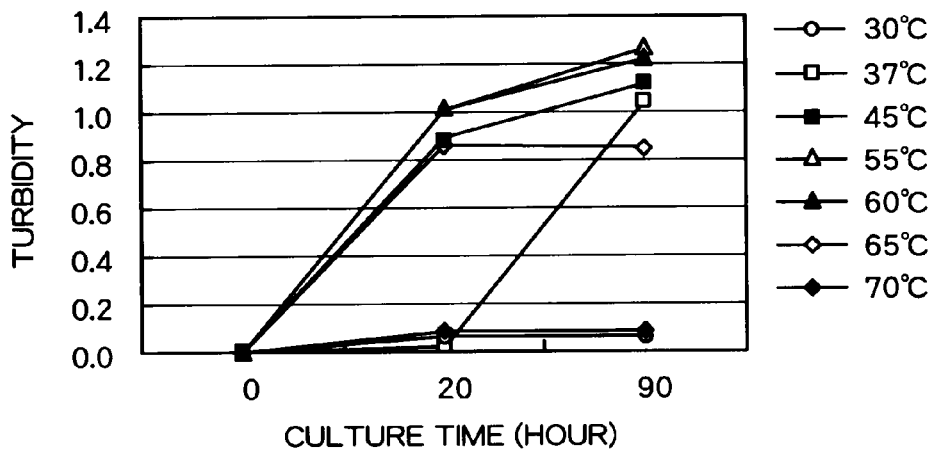
FIG. 6 is a graph showing growth at various temperatures of a microorganism according to one embodiment of the present invention.

FIG. 6 shows the results of determination of the turbidities of the culture solutions obtained through the culture of the strain PEH9 at various temperatures. In FIG. 6, the abscissa axis represents the culture time (hour), the ordinate axis represents the turbidity, the open circles show the determination results at 30° C., the open squares show the determination results at 37° C., the filled squares show the determination results at 45° C., the open triangles show the determination results at 55° C., the filled triangles show the determination results at 60° C., the open rhombuses show the determination results at 65° C., and the filled rhombuses show the determination results at 70° C.

As shown in FIG. 6, the strain PEH9 was found to grow well at temperatures of 45° C., 55° C., 60° C., and 65° C. at culture times of 20 hours and 90 hours, to grow particularly well at 45° C., 55° C., and 60° C., and to grow best at 55° C. and 60° C. Even in the case where the strain PEH9 was cultured at 37° C., the strain grew at a culture time of 90 hours at least as well as the strain cultured at other temperatures. On the other hand, in the cases where the strain PEH9 was cultured at 30° C. and 70° C., the strain did not grow well even at culture times of 20 hours and 90 hours.

Figure 7:
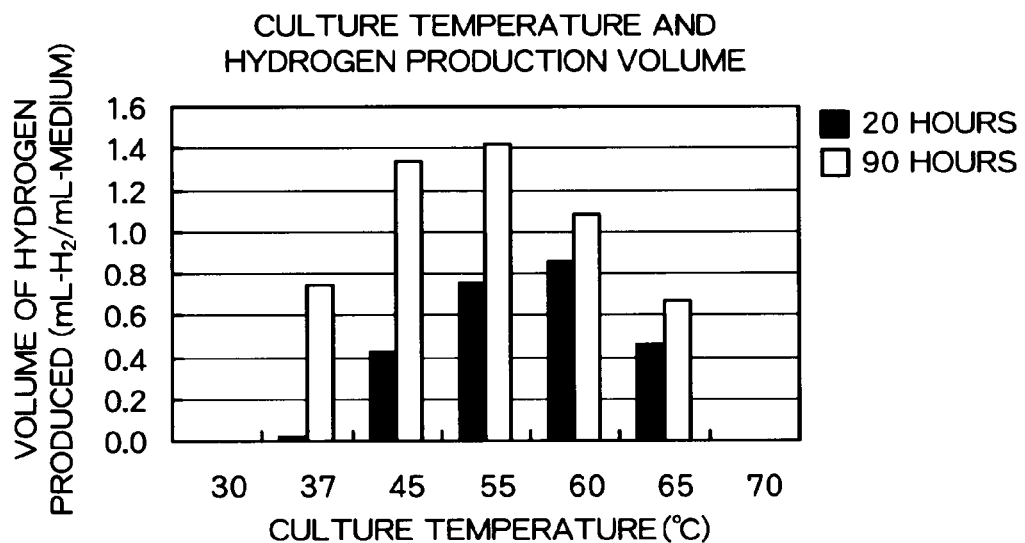
FIG. 7 is a graph showing the hydrogen productivity at various temperatures of a microorganism according to one embodiment of the present invention.

FIG. 7 shows the results of determination of the hydrogen production volumes. In FIG. 7, the abscissa axis represents the culture temperature (° C.), the ordinate axis represents the volume of produced hydrogen per mL of the culture solution (mL-$H_2$/mL-medium), the filled bars show the results of determination of volumes of hydrogen produced in the period from the beginning of culture to 20 hours after the beginning of culture, and the open bars show the results of determination of volumes of hydrogen produced in the period from the beginning of culture to 90 hours after the beginning of culture.

As shown in FIG. 7, the strain PEH9 was able to efficiently produce hydrogen at temperatures of 37° C., 45° C., 55° C., 60° C., and 65° C. Specifically, the hydrogen production volume at the culture time of 20 hours was very small in the case of 37° C., but the hydrogen production volumes in the cases of 45° C. and 65° C. were about the same and larger than the volume in the case of 37° C. In addition, the hydrogen production volume at the culture time of 20 hours was further larger in the case of 55° C. and was the largest in the case of 60° C.

Meanwhile, the hydrogen production volumes at the culture time of 90 hours were about the same in the cases of 37° C. and 65° C., and the hydrogen production volume was larger in the case of 60° C., even larger in the case of 45° C., and largest in the case of 55° C. In the cases of 30° C. and 70° C., little hydrogen was produced at both the culture times of 20 hours and 90 hours.

As described above, the strain PEH9 was able to efficiently produce hydrogen at temperatures in the wide range of 37° C. or higher and 65° C. or lower. Moreover, the strain PEH9 was found to have a high hydrogen producing ability at temperatures in the range of 45° C. or higher and 60° C. or lower, and have a particularly high hydrogen producing ability at a temperature of 55° C.

Example 5

In Example 5, the solubility of a microorganism of the present invention was confirmed. The strain PEH9 was used as the microorganism of the present invention. Meanwhile, a methane microorganism (methane fermentation microorganism group) used for effluent treatment was used as a control. The culture solution used was GBG medium obtained by dissolving 10.00 g of xylose, 4.00 g of yeast extract, 2.50 g of MOPS, 0.91 g of $K_2HPO_4$, 0.30 g of $NaH_2PO_4$, 0.20 g of $MgCl_2.6H_2O$, 0.10 g of $CaCl_2.2H_2O$, 0.30 g of $(NH_4)_2SO_4$, 0.02 g of $FeSO_4.7H_2O$, 0.40 g of L-cysteine, and 1.10 mg of resazurin in 1 L of purified water.

Then, 2.5 L of GBG medium was added to a 5-L continuous culture apparatus (manufactured by ABLE & Biott Co., Ltd.), and the strain PEH9 was inoculated into the medium and cultured while controlling the pH to 5.8 to 6.0 and the temperature to 55° C. On the other hand, the methane microorganism used as a control was cultured while controlling the pH to 7.4 to 7.6 and the temperature to 37° C.

A sample was taken from the culture solution to determine the total sugar amount, and the time when the nutrient (sugar) was exhausted (the time when the xylose content was reduced to 500 mg/L or less) was defined as day 1 of culture, followed by determination of microorganism cell amounts in the culture solution at day 2 and day 7.

The determination of the microorganism cell amounts was performed by: taking 300 mL of the culture solution as a sample; centrifuging the culture solution at 6,000 rpm (round per minute) for 20 minutes; removing the supernatant; washing the microorganism cells with distilled water; centrifuging the mixture again under the same conditions; drying the resultant microorganism cells with heating at 150° C. overnight; and weighing the resultant product. The microorganism cell amount was shown as a relative amount based on the microorganism cell amount at day 1 (defined as 100) (hereinafter, referred to as "residual ratio").

Figure 8:
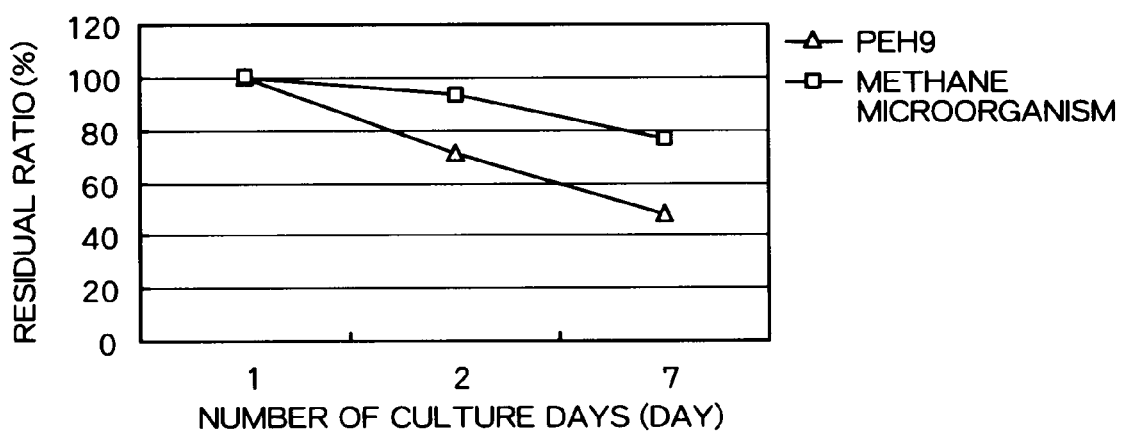
FIG. 8 is a graph showing the autolysis ability of a microorganism according to one embodiment of the present invention.

FIG. 8 shows the results of determination of the microorganism cell amounts. In FIG. 8, the abscissa axis represents the number of culture days (day), the ordinate axis represents the residual ratio (%), the triangles show the results of the strain PEH9, and the squares show the methane microorganism.

As shown in FIG. 8, the microorganism cell amounts of the strain PEH9 were more reduced compared with the methane microorganism at day 2 and day 7 of culture, and the strain was confirmed to easily autolyze. Specifically, the residual ratios of the strain PEH9 at day 2 and day 7 of culture were 72% and 48%, respectively, while the residual ratios of the methane microorganism at day 2 and day 7 of culture were 94% and 77%, respectively.

Example 6

In Example 6, hydrogen fermentation was performed in a medium containing any of various sugars as a single sugar source. The strain PEH9 was used as a microorganism of the present invention. The media used were seven aqueous solutions containing 0.5% (w/v) of xylose, 1.6% (w/v) of tryptone, 1.0% (w/v) of yeast extract, 0.4% (w/v) of sodium chloride, and 2% (w/v) of a sugar selected from glucose, xylose, arabinose, maltose, sucrose, cellobiose, and soluble starch.

Then, the strain PEH9 was inoculated into 20-mL vials each containing 10 mL of the media, and the vials were sealed, followed by batch culture under anaerobic conditions at a temperature of 60° C.

A syringe was injected to each vial 48 hours after the beginning of the culture to calculate a fermentation gas production volume, and the composition of the fermentation gas was determined by gas chromatography in the same way as Example 1, followed by calculation of hydrogen production volumes based on the results of the determination.

As a result, the volumes of hydrogen produced for 48 hours per 10 mL of a culture solution in the cases of using one of glucose, xylose, arabinose, maltose, sucrose, cellobiose, and soluble starch as a sugar source were found to be 7.00 mL, 6.66 mL, 1.75 mL, 6.32 mL, 7.00 mL, 6.70 mL, and 4.10 mL, respectively. Note that the volume of hydrogen produced in a culture solution containing no sugar source was 0.08 mL. As described above, the strain PEH9 was confirmed to consume various sugar sources and produce hydrogen.

Note that the microorganism of the present invention is not limited to the above-mentioned examples. That is, the microorganism of the present invention may be a mutant of the strain PEH9, for example. Examples of a mutagen treatment method for obtaining a mutant include a mutagen treatment by ultraviolet irradiation and a mutagen treatment performed by culturing a microorganism in a medium containing N-methyl-N'-nitro-N-nitrosoguanidine. The mutant is preferably a microorganism that inherits the ability of the strain PEH9 to produce hydrogen efficiently in a low pH range and in a high temperature range.

What is claimed is:

1. A biologically pure microorganism that is a mutant of *Thermoanaerobacterium thermosaccharolyticum* strain identified by accession number FERM BP-10793 having all of the identifying characteristics of said strain FERM BP-10793.

2. The biologically pure microorganism of claim 1, that produces 270 mL or more of hydrogen from 1 g of a sugar when cultured at a pH ranging from pH 5.0 to pH 5.2 at about $10^6$ to $10^7$ cells/ml for 24 hours in a continuous culture under anaerobic conditions at a dilution rate of 0.3 to 0.4.

3. The biologically pure microorganism of claim 1, which produces hydrogen at a molar ratio of 2.1 or more with respect to xylose, when cultured in a medium comprising xylose as a sugar source at a pH ranging from pH 4.8 to pH 5.5 at 55° C. at about $10^6$ to $10^7$ cells/ml for 24 hours in a continuous culture under anaerobic conditions at a dilution rate of 0.2 to 0.4.

4. The biologically pure microorganism of claim 1 that produces more hydrogen when cultured in a medium comprising xylose as a sugar source at a pH of 4.8 to 5.5 at 55° C. at about $10^6$ to $10^7$ cells/ml for 24 hours in a continuous culture under anaerobic conditions at a dilution rate of 0.2 to 0.4 compared to control strain ATCC 7956 when cultured under identical conditions.

5. A method for producing hydrogen comprising fermenting a sugar with the biologically pure strain of claim 1.

6. The method of claim 5, wherein said fermenting the sugar occurs at a pH of 5.5 or lower.

7. The method of claim 5, wherein said fermenting the sugar occurs at a temperature of 55° C. to 60° C.

8. A biologically pure microorganism that is *Thermoanaerobacterium thermosaccharolyticum* identified by accession number FERM BP-10793.

9. A method for producing hydrogen, comprising fermenting a sugar with the biologically pure microorganism of claim 8.

10. The method of claim 9, wherein the fermenting is at a pH of 5.5 or lower.

11. The method of claim 9, wherein the fermenting is at a temperature of 55° C. to 60° C.

\* \* \* \* \*